US012213752B2

(12) United States Patent
Cui

(10) Patent No.: US 12,213,752 B2
(45) Date of Patent: Feb. 4, 2025

(54) ROBOTIC ASSISTED SYSTEM FOR OPHTHALMIC SURGERY

(71) Applicant: Hangzhou Dessight Biomedical Co.,LTD., Zhejiang (CN)

(72) Inventor: Di Cui, Zhejiang (CN)

(73) Assignee: HANGZHOU DESSIGHT BIOMEDICAL CO., LTD., Zhejiang (CN)

( * ) Notice: Subject to any disclaimer, the term of this patent is extended or adjusted under 35 U.S.C. 154(b) by 441 days.

(21) Appl. No.: 17/679,665

(22) Filed: Feb. 24, 2022

(65) Prior Publication Data
US 2023/0233271 A1    Jul. 27, 2023

(30) Foreign Application Priority Data

Jan. 26, 2022 (CN) .......................... 202210095903.7
Jan. 26, 2022 (CN) .......................... 202220236298.6
Jan. 26, 2022 (CN) .......................... 202220260128.1

(51) Int. Cl.
*A61B 34/30* (2016.01)
*A61B 34/00* (2016.01)
(Continued)

(52) U.S. Cl.
CPC .............. *A61B 34/30* (2016.02); *A61B 34/74* (2016.02); *A61B 90/03* (2016.02); *A61F 9/007* (2013.01);
(Continued)

(58) Field of Classification Search
CPC ......... A61B 34/30; A61B 34/74; A61B 90/03; A61B 2090/061; A61B 90/25; A61F 9/007; A61F 9/0008
See application file for complete search history.

(56) References Cited

U.S. PATENT DOCUMENTS

2020/0367977 A1* 11/2020 Liu .................. B25J 9/1676

FOREIGN PATENT DOCUMENTS

| CN | 102438540 B | 6/2014 | |
| CN | 109602499 A * | 4/2019 | ............. A61B 34/37 |

(Continued)

*Primary Examiner* — Tan-Uyen T Ho
*Assistant Examiner* — Khoa Tan Le
(74) *Attorney, Agent, or Firm* — MUNCY, GEISSLER, OLDS & LOWE, P.C.

(57) ABSTRACT

The present invention discloses a robotic assisted system for ophthalmic surgery, comprising a first driving unit, a second driving unit and a third driving unit, wherein the three driving units can respectively complete the movement in three dimensions, the first driving unit is connected with the second driving unit, the second driving unit is connected with the third driving unit, and an instrument is arranged on the third driving unit; during operating, the third driving unit can drive the instrument assembly to move, the second driving unit can drive the third driving unit and instruments thereon to move, and the first driving unit can drive the second driving unit, the third driving unit on the second driving unit and the instruments on the third driving unit to move; the accurate control on the instruments can be completed by controlling the three different driving units. Through the specific RCM structure, the advantages of high precision and compact structure are achieved, and the present invention is suitable for various eye surgeries such as retinal bypass surgery, sub-retina injection and vitrectomy. The ophthalmic surgical device of the present invention has extremely high safety.

18 Claims, 10 Drawing Sheets

(51) Int. Cl.
*A61B 90/00* (2016.01)
*A61B 90/25* (2016.01)
*A61F 9/00* (2006.01)
*A61F 9/007* (2006.01)

(52) U.S. Cl.
CPC ......... *A61B 2090/061* (2016.02); *A61B 90/25* (2016.02); *A61F 9/0008* (2013.01)

(56) References Cited

FOREIGN PATENT DOCUMENTS

| | | | | |
|---|---|---|---|---|
| CN | 110384555 A | * | 10/2019 | ............. A61B 34/30 |
| CN | 211867811 U | * | 11/2020 | |

* cited by examiner

ROBOTIC ASSISTED SYSTEM FOR OPHTHALMIC SURGERY

CROSS-REFERENCE TO RELATED APPLICATIONS

This application claims the priority of Chinese application No. 202210095903.7 filed Jan. 26, 2022; Chinese application No. 202220236298.6 filed Jan. 26, 2022 and Chinese application No. 202220260128.1 filed Jan. 26, 2022, which is incorporated herein by reference in its entirety, including the description, claims and drawings.

FIELD OF THE INVENTION

The present invention relates to the field of medical instruments, and particularly relates to an robotic assisted system for ophthalmic surgery and ophthalmic surgery equipment comprising same.

BACKGROUND OF THE INVENTION

The following description of the Background Art is only to help readers understand the present invention, and does not constitute the prior art of the present invention or has any limitation to the present invention.

The eyeballs are small in size, and their tissue structure is delicate and fragile. Ophthalmic surgery requires extremely high precision requirements, and it is difficult for human hands to achieve the precision requirements of surgical operations. For example, in the operation of retinal vein occlusion disease, the diameter of the blood vessels on the retina is about 80 µm, and the average amplitude of hand tremors of ophthalmologists reaches 156 µm, which cannot meet the requirements of surgical precision.

The use of robotic-assisted surgery has obvious advantages in operation sensitivity, stability and accuracy. It can not only avoid the tremor of the human hands, but also enhance the doctor's perception ability, thereby improving the safety of the operation, which has important research significance and application value. At present, the Chinese patent CN102438540B provides a remote motion center locator, but its structure is complicated, and some joint transmissions use belt transmission, which has relatively low precision, and is not compact in size, making it difficult to miniaturize.

This proposes higher requirements for the precision of surgical robots.

SUMMARY OF THE INVENTION

The present invention aims to provide a robotic assisted system for ophthalmic surgery and ophthalmic surgery equipment comprising an robotic assisted system for ophthalmic surgery, so as to solve the problem of insufficient precision proposed in the Background Art.

In order to achieve the above purpose, the technical solution adopted by the present invention is that an robotic assisted system for ophthalmic surgery comprises a first driving unit, a second driving unit and a third driving unit, wherein the three driving units can respectively complete the movement in three dimensions; the first driving unit is connected with the second driving unit; the second driving unit is connected with the third driving unit; and an instrument assembly or a mechanical structure for performing ophthalmic surgery is arranged on the third driving unit.

During working or actual operation, the third driving unit can drive the instrument assembly to move on the eyes, the second driving unit can drive the third driving unit and instruments thereon to move, and the first driving unit can drive the second driving unit, the third driving unit on the second driving unit and the instruments on the third driving unit to move, such that accurate control on the instruments can be completed by controlling the three different driving units.

Further, the first driving unit can provide rotation motion in one direction such that the instrument assembly can rotate.

The first driving unit comprises a base, a first power element is mounted on the base, the output end of the first power element is connected with a connecting piece, the connecting piece is connected with a pedestal, the pedestal is used for being mounted on a second driving element, and the pedestal can rotate by controlling the first power element to work.

The first driving unit is provided with a first speed reducer in a matched mode, and the first speed reducer is mounted between the connecting piece and the first power element.

The first speed reducer is a harmonic speed reducer.

The base is in a U shape, the two ends of the pedestal are connected to the U-shaped base through connecting pieces, the connecting position on one side is provided with power output of the first power element, and the connecting position on the other side is provided with a bearing.

A balancing weight is mounted on the connecting piece close to one side of the bearing.

Further, the second driving unit comprises an RCM structure, the structure comprises a first quadrilateral structure and a second quadrilateral structure, wherein the first quadrilateral structure and the second quadrilateral structure have a common overlapping vertex, the vertex defines two sides of the first quadrilateral structure and two sides of the second quadrilateral structure, the first quadrilateral structure comprises a second connecting rod and a third connecting rod which are located at the position of the overlapping vertex and connected with the overlapping vertex, and the second quadrilateral structure comprises a fourth connecting rod and a sixth connecting rod which are located at the position of the overlapping vertex and connected with the overlapping vertex; and the third connecting rod and the fourth connecting rod are integrally formed, and the sixth connecting rod and the second connecting rod are integrally formed.

The first quadrilateral structure comprises a second connecting rod, a third connecting rod, a first connecting rod and a seventh connecting rod, wherein the second connecting rod and the third connecting rod are connected and hinged through overlapped vertexes; the third connecting rod and the first connecting rod are connected and hinged through a first vertex; the seventh connecting rod comprises a base; the base is hinged to the second connecting rod and the first connecting rod respectively; the hinged positions are a second vertex and a third vertex respectively; the part, positioned between the second vertex and the third vertex, on the base is the seventh connecting rod.

The second quadrilateral structure comprises a sixth connecting rod, a fourth connecting rod, a fifth connecting rod and an eighth connecting rod; the fourth connecting rod and the sixth connecting rod are connected and hinged through overlapped vertexes; the fifth connecting rod and the sixth connecting rod are connected and hinged through a fourth vertex; the eighth connecting rod comprises a tail end mounting frame; the tail end mounting frame is hinged to the fourth connecting rod and the fifth connecting rod respectively; the hinged positions are a fifth vertex and a sixth vertex respectively; the part, positioned between the fifth vertex and the sixth vertex, on the tail end mounting frame is the eighth connecting rod.

The second driving unit comprises at least one group of RCM structures consisting of the first quadrilateral structure and the second quadrilateral structure, and the RCM structures move synchronously.

In two adjacent groups of RCM structures, corresponding connecting rods are connected through supporting rods.

Or, a connecting plate for connecting the connecting rods is arranged between the corresponding connecting rods, and the connecting plate and the corresponding connecting rod are integrally formed.

The second driving unit further comprises a second power element, power input is performed on the RCM structures through the second power element to complete motion control of the RCM structures, and the motion of the first quadrilateral structure is controlled through the second power element, such that the motion of the second quadrilateral structure is driven, and the motion of the instrument is adjusted.

The second driving unit adopts an indirect control mode on the first quadrilateral structure.

The second power element is in power connection with a first lead screw through a first coupling, a first sliding block is arranged on the first lead screw, a driving rod is hinged to the first sliding block, one end of the driving rod is hinged to the first sliding block, and the other end of the driving rod is hinged to a certain position on the first quadrilateral structure, thus the second power element can drive the first quadrilateral structure to move.

Further, the third driving unit is mounted on the tail end mounting frame, and the third driving unit can perform linear control on the instrument.

A second screw rod is arranged on the tail end mounting frame, a second sliding block is mounted on the second screw rod, an instrument mounting bracket is mounted on the second sliding block, and the instrument mounting bracket is used for mounting the instrument.

The second screw rod is driven by a third power element, and the third power element is indirectly connected through a gear set.

The power output end of the third power element is connected with a first gear, the first gear is meshed with a second gear, and the axis position of the second gear is connected with the second screw rod through a coupling.

Further, a surgery robot comprises a sensing unit, and the sensing unit is used for identifying the distance between the RCM structure position on the surgery robot and other objects except a patient.

Ophthalmic surgery equipment comprises an robotic assisted system for ophthalmic surgery and further comprises a main console, wherein the main console can be used for controlling the surgery robot to move, the main console is connected with a control handle, an operator controls the surgery robot to work by operating the control handle, the main console is further connected with a pedal, and the pedal can be used for enabling control over the control handle and the surgery robot and/or speed ratio adjustment of the control handle and the surgery robot.

Further, the surgery robot comprises a sensing unit, the sensing unit is used for identifying the distance between the position of the RCM structure on the surgery robot and other objects except a patient, the surgery robot is provided with a safe distance, when the sensing unit identifies that the distance between the RCM structure and an obstacle is smaller than a preset safe distance, the control handle vibrates and/or equipment gives out an alarm, and meanwhile the control handle temporarily shields the function of controlling the surgery robot to move.

Further, the control handle is provided with a button, namely a continuous working button, when the handle vibrates and/or the equipment gives out an alarm, the robot stops moving, the control handle is shielded, and if an operator clicks the continuous working button, the surgery robot can continue to move according to a command of the control handle.

When the distance between the RCM structure and other objects is smaller than the preset safety distance, the load of the control handle is increased, the movement speed of the control handle is decreased, and correspondingly, the movement speed of the RCM structure is decreased; when the distance between the RCM structure and other objects is larger than the safety distance, the control handle restores an original control mode.

Further, the surgery robot has a minimum distance, the minimum distance is smaller than the safe distance, when the distance between the RCM structure and other objects is smaller than or equal to the preset minimum distance, the control handle is locked, the control handle cannot continue to move under the operation of the operator, and the RCM structure cannot move.

Meanwhile, the equipment gives an alarm, after a period of time, the control handle returns to the initial position, and the surgery robot returns to the initial position.

Further, the control handle is provided with a button, namely a route recalculation button; when the handle vibrates and/or the equipment gives out an alarm sound, the surgery robot stops moving and waits for an instruction of the operator; if the operator clicks the route recalculation button, the robot stops for a period of time and recalculates different movement routes when the tail ends of instruments are located at the same position; under the routes, the RCM structure does not touch the obstacle and enough safety distance is kept.

When the robot cannot calculate one route meeting the safety distance, the equipment gives out the rapid alarm sound; after a period of time, the control handle is recovered to an initial position and the surgery robot is also recovered to the initial position.

After the routes are calculated, the routes are displayed on the main console; the operator selects the proper route by self and then the surgery robot automatically moves according to the calculated route; in the process, the control handle cannot be operated.

The present invention has the advantages that the robotic assisted system for ophthalmic surgery is provided, through the specific RCM structure, the advantages of high precision and compact structure are achieved, and the robotic assisted system for ophthalmic surgery is suitable for various eye surgeries such as retinal bypass surgery, sub-retina injection and vitrectomy; through the RCM structure, a far-end movement center point can be provided, the far-end movement center point coincides with a minimally invasive surgery incision, it can be guaranteed that a surgical instrument and the surgery incision of the patient are not pulled in the minimally invasive surgery process, the surgery safety is guaranteed, and the surgery requirements are met; in addition, the robotic assisted system for ophthalmic surgery equipment is small in size, can be conveniently used in cooperation with other matched equipment, and cannot collide with a microscope, and the microscope does not need to be frequently moved away in the surgery process.

DETAILED DESCRIPTION

Figure 1:
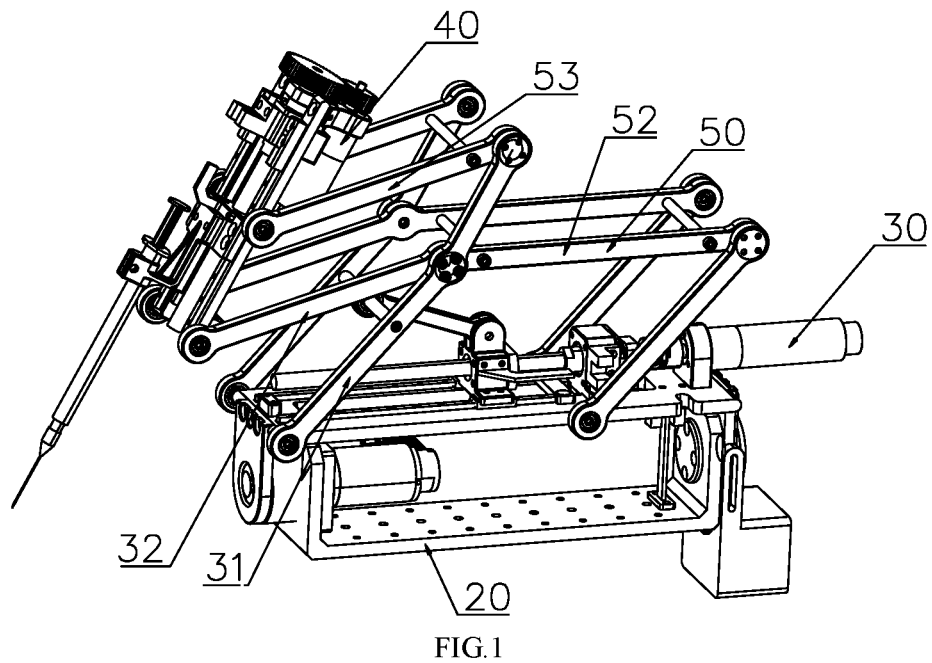
FIG. 1 is an overall structural schematic diagram of the present invention.

The embodiments of the present invention will be further described in detail below in conjunction with the accompanying drawings. It should be noted that the embodiments are only a detailed description of the present invention, and should not be regarded as a limitation of the present invention. All features or all methods or process steps disclosed in the embodiments of the present invention can be combined in any way except mutually exclusive features and/or steps.

An robotic assisted system for ophthalmic surgery comprises a first driving unit 20, a second driving unit 30 and a third driving unit 40, wherein the three driving units can respectively complete the movement in three dimensions, so that the robotic assisted system for ophthalmic surgery can meet the requirement on flexibility; the first driving unit 20 is connected with the second driving unit 30; the second driving unit 30 is connected with the third driving unit 40; an instrument 60 is arranged on the third driving unit 40; in the work process, the third driving unit 40 can drive the instrument 60 to do vertical movement; the second driving unit 30 can drive the third driving unit 40 and the instrument 60 arranged on the third driving unit to do forward and backward movement; the first driving unit 20 can drive the second driving unit 30 and the third driving unit 40 and the instrument 60 arranged on the second driving unit to move. Therefore the three different driving units are controlled; the precise control on the instrument 60 can be completed; particularly, the precise control on the tail end 70 of the instrument 60 can be completed. The final instrument assembly is provided with an element used for performing surgery on the eyes; through the cooperated control of the three units, the rotation movement, the vertical movement, the forward and backward movement and the leftward and rightward movement of the instrument 60 can be realized, so that the rotation can be realized; the movement in a tiny range on the eyes can be improved. The followings are the specific description.

First Driving Unit

The first driving unit 20 serves as a first-level power unit and can drive the second driving unit 30, the third driving unit 40 on the second driving unit and an instrument 60 located on the third driving unit to move. In order to control the instrument 60 conveniently, the first driving unit 20 preferably can provide rotation movement in one direction. Specifically, the first driving unit 20 comprises a base 11, a first power element 21 is mounted on the base 11, the output end of the first power element 21 is connected with a connecting piece 24, the connecting piece 24 is connected with a pedestal 51, and the pedestal 51 is used for mounting the second driving unit 30. In this way, by controlling the first power element 21 to work, rotation of the pedestal 51 can be achieved, and in other words, rotation of a robot in one direction is controlled.

Figure 2:
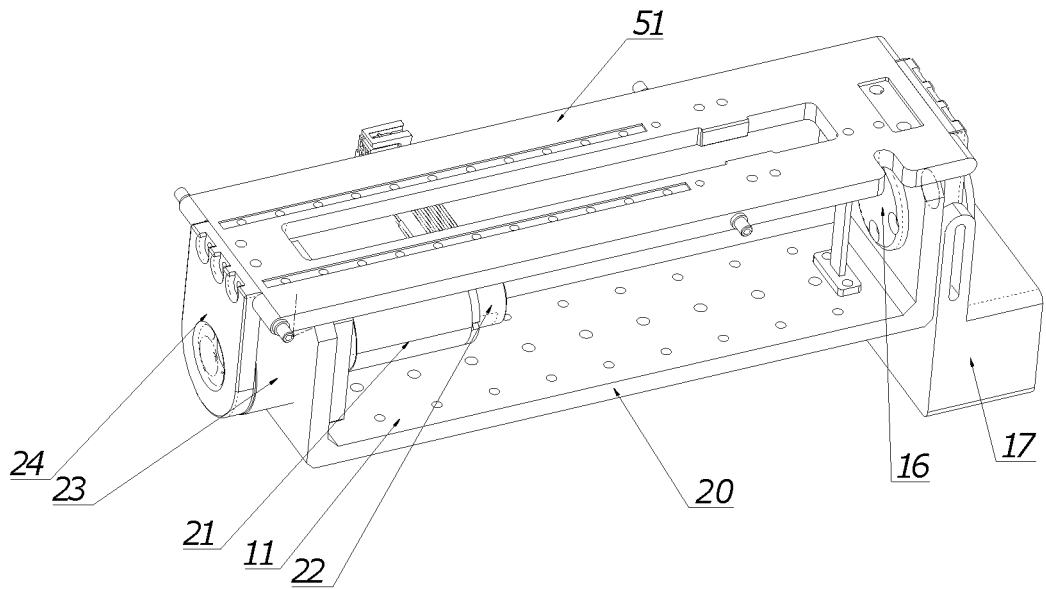
FIG. 2 is a structural schematic diagram of a first driving unit of the present invention.

Preferably, in order to ensure the movement stability of the pedestal 51, the base 11 is U-shaped, the two ends of the pedestal 51 are connected to the U-shaped base 11 through connecting pieces 24, the connecting position on one side is provided with power output of the first power element 21, so that the first power element 21 can drive the pedestal 51 to rotate, and the connecting position on the other side is provided with a bearing 16 so as to facilitate rotation of the pedestal 51. The rotation is generally performed around the bearing 16 as the circle center, the base is driven to rotate, all structures located on the base can be driven to rotate as a whole, and the rotation direction is shown in the arrow direction shown in the FIG. 2. It can be understood that the power element 21 drives the connecting pieces 24 to rotate through rotation, thus the pedestal 51 is driven to rotate, and the rotation can be clockwise or anticlockwise or can be interchangeable rotation movement in the two directions.

Preferably, the first driving unit 20 is matched with a first speed reducer 23, the first speed reducer 23 is mounted between a connecting piece 24 and the first power element 21, and the first speed reducer 23 can reduce the rotating speed output by the first driving unit 20. Further, the first speed reducer 23 is a harmonic speed reducer and can eliminate gear intermittence of mechanical movement. In the traditional technology, a stepping motor is usually used for directly completing transmission, movement of a mechanical element is driven by means of movement of a mechanical gear, after multiple times of movement, gaps between machines are accumulated, and therefore errors are larger. According to the present invention, the harmonic speed reducer is adopted, mechanical errors can be eliminated, and therefore rotation is more accurate.

Preferably, a balancing weight 17 is mounted on the connecting piece 24 close to one side of the bearing 16. The balancing weight 17 can play a role in balancing the load of the first power element 21, and therefore the service life of the first power element 21 is prolonged, and power output of the first power element 21 is accurate.

Second Driving Unit

The second driving unit 30 is mounted on the pedestal 51. The second driving unit 30 comprises an RCM structure, the structure comprises a first quadrilateral structure 52 and a second quadrilateral structure 53, wherein the first quadrilateral structure 52 and the second quadrilateral structure 53 have a common overlapping vertex 54, the vertex defines two sides of the first quadrilateral structure 52 and two sides of the second quadrilateral structure 53, the first quadrilateral structure 52 comprises a second connecting rod 522 and a third connecting rod 523 which are located at the position of the overlapping vertex 54 and connected with the overlapping vertex 54, and the second quadrilateral structure 53 comprises a fourth connecting rod 531 and a sixth connecting rod 533 which are located at the position of the overlapping vertex 54 and connected with the overlapping vertex 54. The third connecting rod 523 and the fourth connecting rod 531 are integrally formed, and the sixth connecting rod 533 and the second connecting rod 522 are integrally formed. The integral forming means that the two sides are actually formed at one time, and also means that the connection relationship of the two sides is not the relationship of movable connecting but is fixed connecting. The fixed connecting means that the two sides are connected together and are fixed without change, and the degree of an included angle formed between the two sides is fixed. The fixation is an antonym of the movement, and the position of the two sides connected together is fixed.

Preferably, the third connecting rod 523 and the fourth connecting rod 531 are connected together to form a straight line, and the sixth connecting rod 533 and the second connecting rod 522 are connected together to form a straight line, or the third connecting rod 523 and the fourth connecting rod 531 are connected together to form a non-straight line, and the sixth connecting rod 533 and the second connecting rod 522 are connected together to form a non-straight line, for example, the third connecting rod 523 and the fourth connecting rod 531 form a certain angle with a common vertex, and the sixth connecting rod 533 and the second connecting rod 522 form a certain angle with a common vertex. Certainly, the fixed angles can be continuously changed along with different designs, for example, the angles are obtuse angles, and the value ranges of the angles are [120°-180°).

Preferably, the included angle between the third connecting rod 523 and the fourth connecting rod 531 is the same as the included angle between the sixth connecting rod 533 and the second connecting rod 522.

Preferably, the third connecting rod 523 and the fourth connecting rod 531 form a first combined connecting rod 32, the sixth connecting rod 533 and the second connecting rod 522 form a second combined connecting rod 31, and the first combined connecting rod 32 and the second combined connecting rod 31 are hinged through an overlapped vertex 54. That is, the first combined connecting rod 32 and the second combined connecting rod 31 are movably connected, and in the working process of the RCM structure, the included angle between the first combined connecting rod 32 and the second combined connecting rod 31 can be changed.

Preferably, the first quadrilateral structure 52 comprises the second connecting rod 522, the third connecting rod 523, a first connecting rod 521 and a "seventh connecting rod", the second connecting rod 522 and the third connecting rod 523 are connected and hinged through the overlapped vertex 54, and the third connecting rod 523 and the first connecting rod 521 are connected and hinged through a first vertex 61; the "seventh connecting rod" comprises the pedestal 51, the pedestal 51 is hinged to the second connecting rod 522 and the first connecting rod 521, the hinge positions are a second vertex 62 and a third vertex 63 respectively, and the part, located between the second vertex 62 and the third vertex 63, of the pedestal 51 is the "seventh connecting rod". The "hinge" means that the two rods can be movably connected around a connecting point, are generally connected in a rotating mode, and the rotating connecting is on the contrary of the fixed rotating of the sixth connecting rod 533 and the second connecting rod 522.

Preferably, the second quadrilateral structure 53 comprises a fifth connecting rod 532 and an "eighth connecting rod" besides the sixth connecting rod 533 and the fourth connecting rod 531, the fourth connecting rod 531 and the sixth connecting rod 533 are connected and hinged through the overlapping vertex 54, the fifth connecting rod 532 and the sixth connecting rod 533 are connected and hinged through a fourth vertex 64, the "eighth connecting rod" comprises a tail end mounting frame 534, the tail end mounting frame 534 is hinged to the fourth connecting rod 531 and the fifth connecting rod 532, the hinged positions are a fifth vertex 65 and a sixth vertex 66, and the part, located between the fifth vertex 65 and the sixth vertex 66, of the tail end mounting frame 534 is the "eighth connecting rod".

In the technical solution of the present invention, besides the common vertex, the angle between the connecting edges of the other three vertexes of the first quadrangle and the other three vertexes of the second quadrangle and the remaining vertexes can be adjusted at will. In the movement process of the RCM structure, the movement of one edge (connecting rod) can drive the other edges (connecting rods) to move together, the position relation between the edges (connecting rods) is that the edges correspond to one another, and therefore an instrument 60 connected to the second quadrilateral structure can move tightly, and control precision is improved. In another aspect, the RCM structure designed according to the technical solution can be miniaturized and compacted due to its foldability, and it is very useful in surgery, especially ophthalmic surgery, due to the fact that a microscope is needed for use in cooperation with conventional ophthalmic surgery, when the RCM structure is large, no enough space is available for developing the microscope, the risk of surgery is increased, and the present invention can well solve the problem. In addition, in light of the movement dimension of the instrument 60 (generally a scalpel for ophthalmic surgery or other tools directly acting on eyes), the second driving unit 30 of the present invention can adjust the angle of the instrument 60 and control the left-right movement of the tail end 70, and the tail end 70 can be kept still under the condition that the instrument 60 moves conveniently.

Preferably, the first quadrilateral structure 52 and the second quadrilateral structure 53 are both parallelogram structures. That is, in the same quadrangle, the lengths of opposite sides are equal, for example, the length of the "eighth connecting rod" is equal to the length of the sixth connecting rod 533; the length of the fifth connecting rod 532 is equal to the length of the fourth connecting rod 531; and the length of the first connecting rod 521 is equal to the length of the second connecting rod 522.

Figure 3:
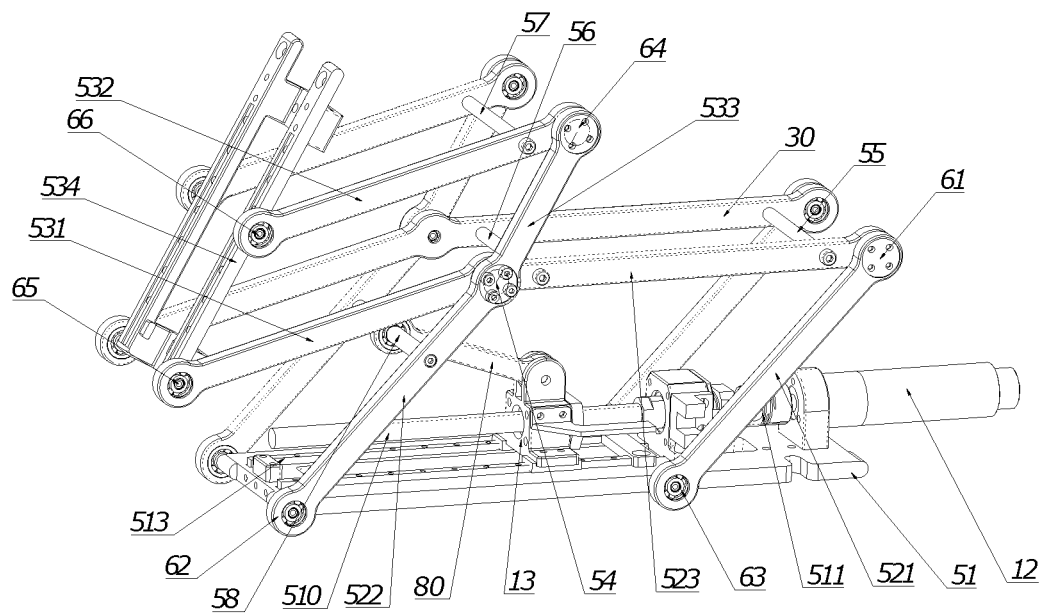
FIG. 3 is a structural schematic diagram of a second driving unit of the present invention.
Figure 6:
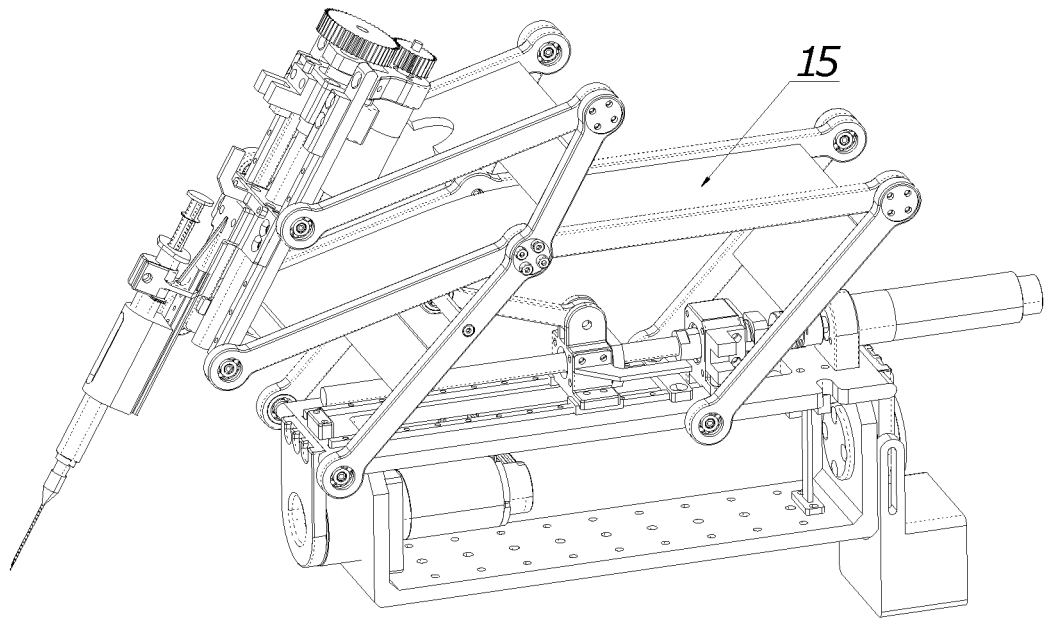
FIG. 6 is another overall structural schematic diagram of the present invention.

Preferably, the second driving unit 30 comprises at least one group of RCM structures consisting of the first quadrilateral structure 52 and the second quadrilateral structure 53, and the RCM structures move synchronously, so that the third driving unit 40 mounted on the second driving unit 30 can be mounted firmly, and the second driving unit 30 moves stably when driving the third driving unit 40. For example, in FIG. 3, two groups of RCM structures are arranged in the second driving unit 30, corresponding connecting rods in two adjacent groups of RCM structures are connected through supporting rods, specifically, a first supporting rod 55 is arranged between two third connecting rods 523, a fourth supporting rod 58 is arranged between two second connecting rods 522, a second supporting rod 56 is arranged between two sixth connecting rods 533, and a third supporting rod 57 is arranged between two fifth connecting rods 532. By adding the supporting rods, better linkage among different groups of RCM structures can be kept. Further, according to FIG. 6, in the two groups of RCM structures, a connecting plate 15 for connecting the connecting rods is arranged between the corresponding connecting rods (for example, a connecting plate is arranged between two first combined connecting rods 32), and the connecting plate 15 and the corresponding connecting rod are integrally formed, so that the rigidity of the connecting rods can be improved, and meanwhile, the assembling is convenient. In addition, by means of the mode, perfect linkage among different groups of RCM structures can be realized. Certainly, the connecting plate and the corresponding two connecting rods are integrally formed so that the whole can be regarded as the same group of RCM structures, and the system is different from a traditional RCM structure and has two hinge points based on one position.

Figure 7:
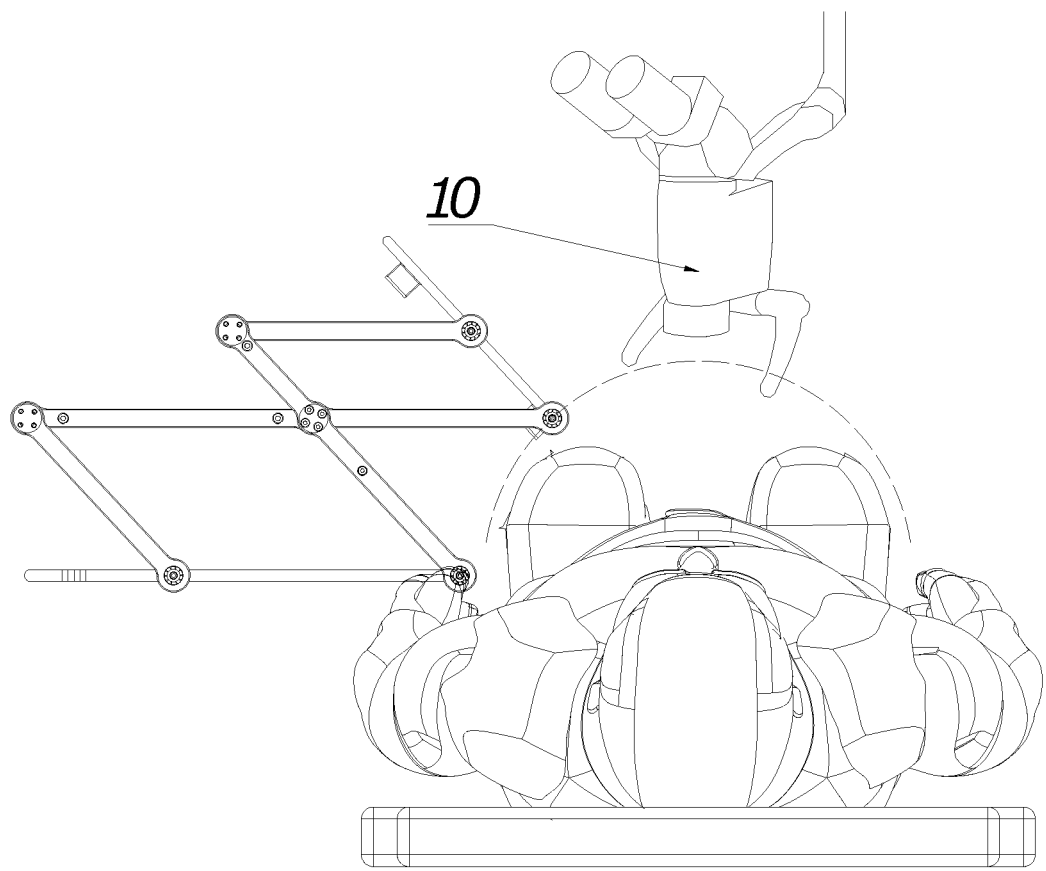
FIG. 7 is a schematic diagram of a conventional RCM structure during collision with a microscope.

In addition, in the design process of the RCM structure for ophthalmic surgery, the RCM structure is not simple and is designed at will, the size calculation and the connecting rod angle of the RCM structure need to be calculated in a large amount. When the robot is applied to the ophthalmic surgery, the robot is used for assisting the surgery, a microscope needs to be used in cooperation, the robotic assisted system for ophthalmic surgery which is not subjected to structure optimization can easily interfere with the microscope, that is, the robotic assisted system for ophthalmic surgery can easily collide with the microscope in the working process, in order to avoid the interference problem, sometimes, the microscope needs to be frequently moved away or back in the surgery process, the operation in the surgery can be interrupted, the surgery time is prolonged, and for example, as shown in the FIG. 7, the RCM structure can collide with the microscope 10.

Figure 8:
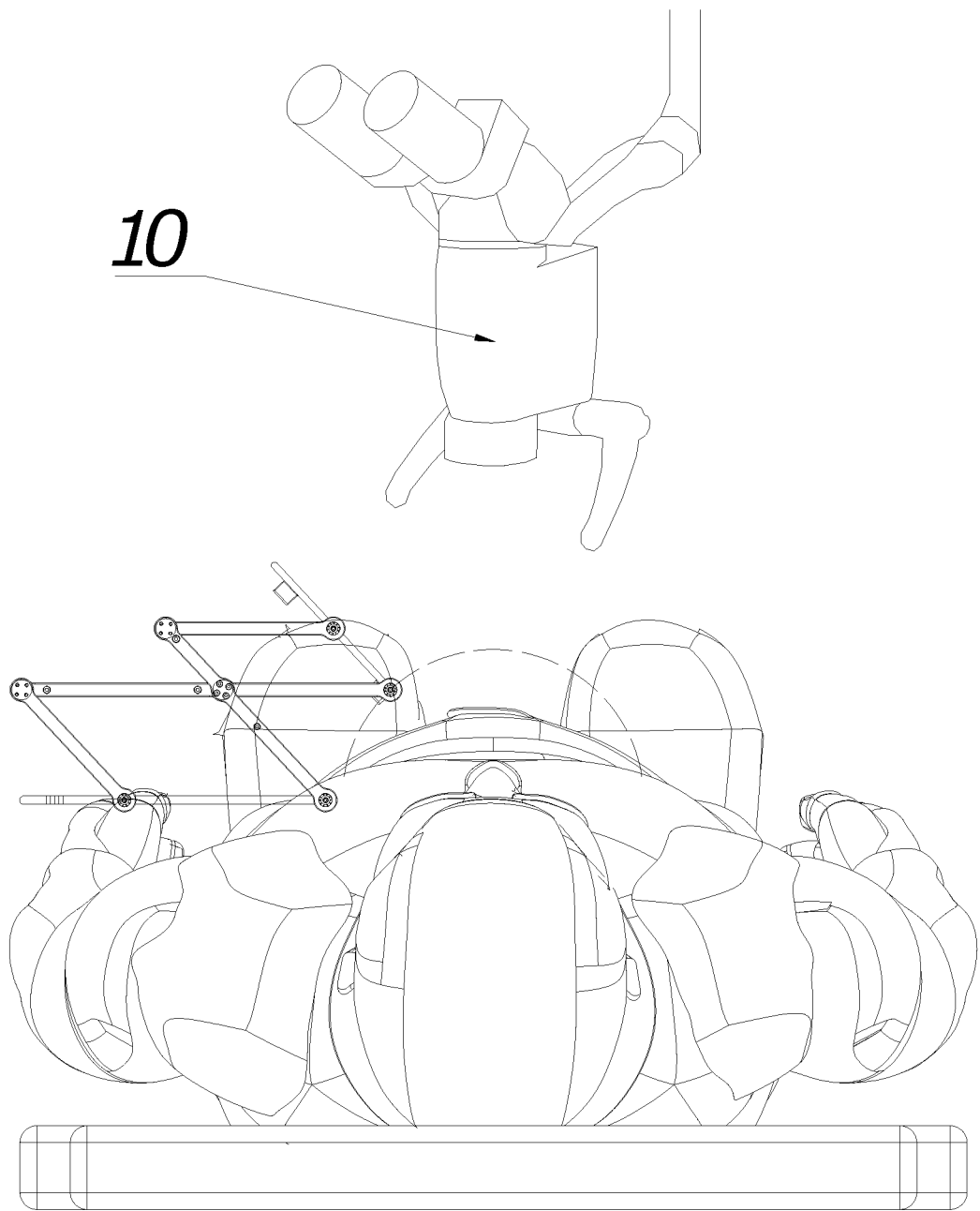
FIG. 8 is a working state schematic diagram of a miniaturized RCM structure.
Figure 9:
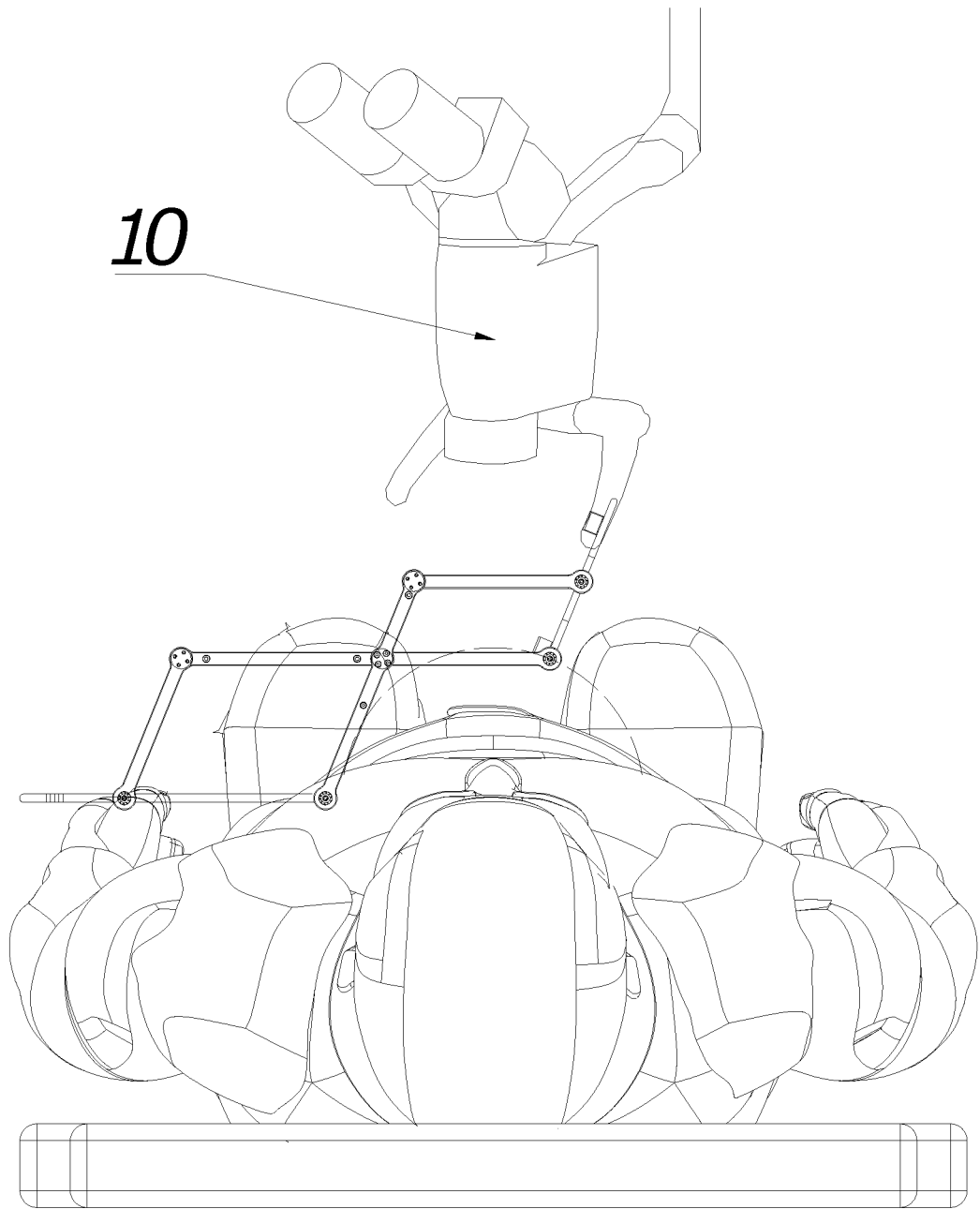
FIG. 9 is another working state schematic diagram of a miniaturized RCM structure.
Figure 10:
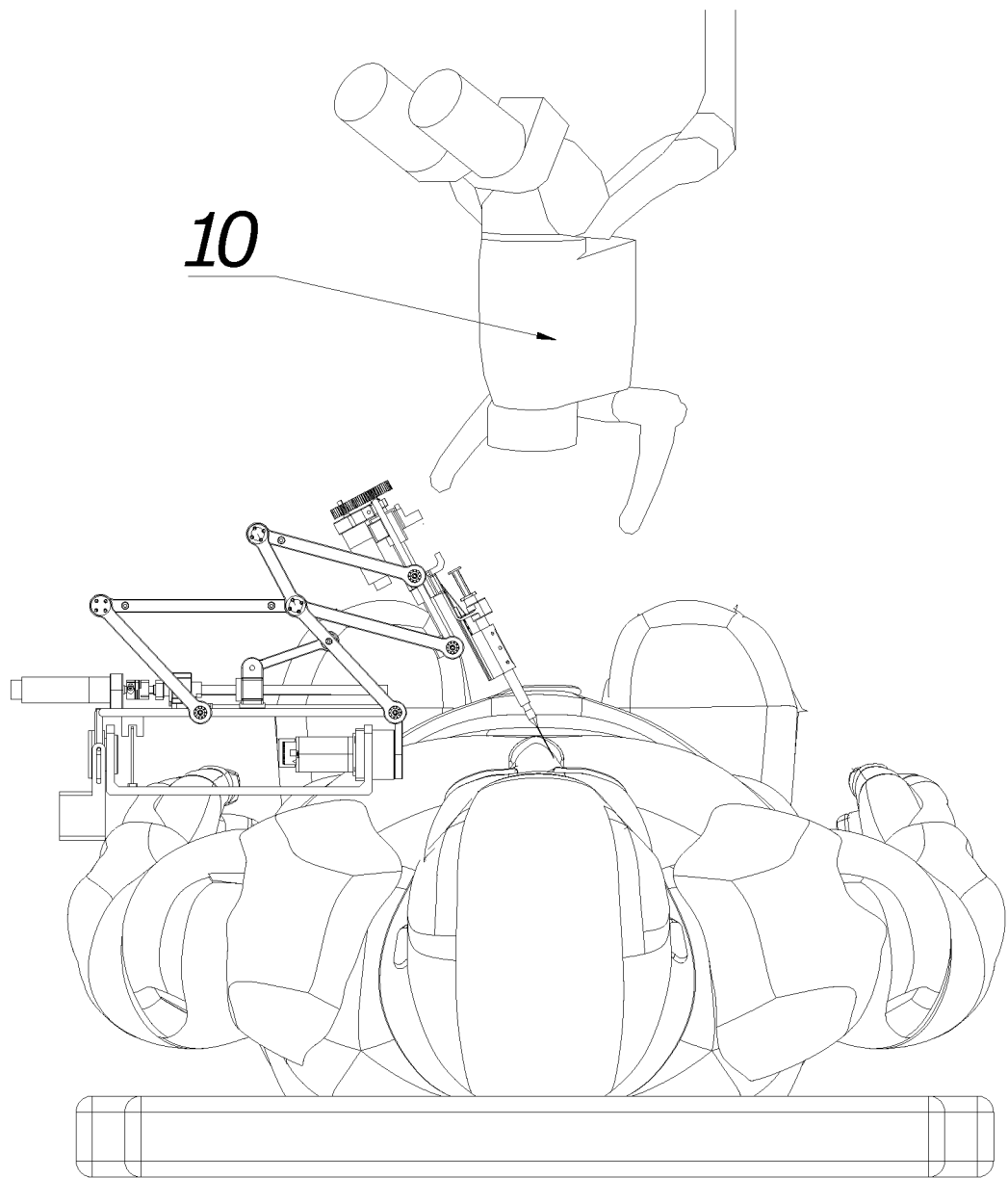
FIG. 10 is a working state schematic diagram of an RCM structure during surgery of the right eye of a patient.

In some ways, miniaturization and optimization design are conducted on the RCM structure so that the RCM structure does not collide with the microscope 10 in the movement process, and according to the FIG. 8, the RCM structure shown in the FIG. 8 does not collide with the microscope 10 in the movement process. However, the RCM structure still has the problems that in the state shown in the FIG. 8, the RCM structure can be aligned with the left eye of a patient for surgery, and the microscope 10 is not shielded in the state; when the RCM structure needs to conduct surgery on the right eye of the patient, the state shown in the FIG. 9 is changed by driving the RCM structure to move, in the state, the RCM structure does not collide with the microscope 10, but the sight of the microscope 10 is blocked, and the surgery process is affected.

Figure 12:
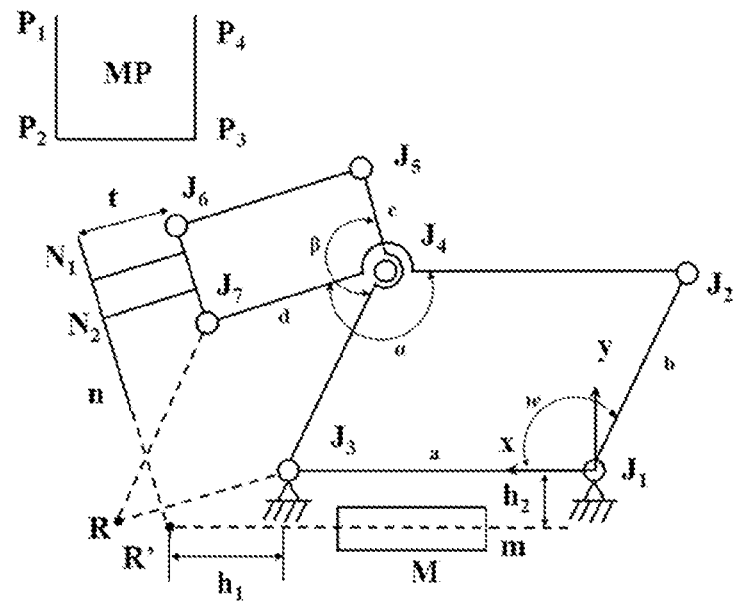
FIG. 12 is a structure diagram of a robot.

In order to solve the problem, a large amount of calculation and motion simulation are carried out, and the specific calculation process is as follows:

FIG. 12 is the structure diagram of the robot and is marked for each important point on the structure diagram, and MP(P1P2P3P4) in the diagram represents the area of the microscope 10. The intersection point of the extension line of the axis N1N2 where the tail end 70 of the instrument 60 is located and the axis of the first power element 21 is an R line, and is defined as a target RCM point, namely an RCM point meeting the design requirement. The actual RCM of the robot of the double-parallelogram mechanism in the current state is R, and one target of optimizing the RCM structure is to enable the actual RCM to coincide with the target RCM point so as to meet the design requirement of the robot. The target RCM point mainly has two requirements: the first requirement is that the R' position falls on the intersection point of the axis m of the first power element 21 and the axis N1N2 of a needle, thus the trauma to the eyeball entering point in the operation process can be reduced. J1 is used as a coordinate origin, a coordinate system is established, the length of each side of the double-quadrangle mechanism is shown in the FIG. If R' (x', y'), R' (h1+a, −h2), wherein h1 is the x-axis projection distance from R' to the joint point J3, and h2 is the y-axis projection distance from R' to the joint point J3. In order to ensure that the robot can perform an operation on the left eye and the right eye and does not interfere with the side face of the person:

R' (x', y'), it is:

$$\begin{cases} x' = a - c \cos \alpha \\ y' = -c \cos \alpha \end{cases}$$

J5 (x1, y1), J6(x2, y2), N1(x3, y3) is defined;
According to:

$$\begin{cases} \vec{J_1 J_5} = \vec{J_1 J_2} + \vec{J_2 J_4} + \vec{J_4 J_5} \\ \vec{J_1 J_6} = \vec{J_1 J_2} + \vec{J_2 J_4} + \vec{J_4 J_5} + \vec{J_5 J_6} \\ \vec{J_1 N_1} = \vec{J_1 J_2} + \vec{J_2 J_4} + \vec{J_4 J_5} + \vec{J_5 J_6} + \vec{J_6 N_1} \end{cases}$$

Then:

$$\begin{cases} x_1 = a + b \cos \omega - d \cos(\beta + \omega) \\ y_1 = b \sin \beta - d \sin(\beta + \omega) \\ x_2 = a + b \cos \omega - c \cos \alpha - d \cos(\beta + \omega) \\ y_2 = b \sin \beta - c \sin \alpha - d \sin(\beta + \omega) \\ x_3 = a + b \cos \omega - c \cos \alpha - (d + t) \cos(\beta + \omega) \\ y_3 = b \sin \beta - c \sin \alpha - (d + t) \sin(\beta + \omega) \end{cases}$$

It is required that in the movement process, along with ω changes, a J5track, a J6track and an N1 track do not interfere with a microscope area MP.

Parameters (a, b, c, d, α, β and t) of a double-parallel four-bar mechanism meet the following conditions that (1) the actual RCM and the target RCM coincides, namely R=R'(2)J5, and the J6 track and the N1 track do not interfere with the microscope area MP, namely J5, J6, N1∉MP.

Through the calculation process, a connecting rod combination with a good RCM structure internal dimension is finally designed. The length of the third connecting rod 523 is the same as the length of the seventh connecting rod (located between the second vertex 62 and the third vertex 63) on the control pedestal 51, the ratio of the first connecting rod 521 to the seventh connecting rod is 1:2-7:8, the length of the first connecting rod 521 is the same as that of the second connecting rod 522, the ratio of the sixth connecting rod 533 to the second connecting rod 522 is 1:4-3:4, the length of the eighth connecting rod (located between the fifth vertex 65 and the sixth vertex 66) on the tail end mounting frame 534 is the same as that of the sixth connecting rod 533, the ratio of the fourth connecting rod 531 to the third connecting rod 523 is 3:4-11:12, and the length of the fifth connecting rod 532 is the same as that of the fourth connecting rod 531. The included angle between the second connecting rod 522 and the sixth connecting rod 533 in the first combined connecting rod 31 ranges from 120° to 175°, and the included angle between the fourth connecting rod 531 and the third connecting rod 523 in the second combined connecting rod 32 ranges from 120° to 175°. Due to the arrangement of the connecting rods of different ratios, the movement track of the instrument can be affected, and the movement precision of the instrument can also be affected. Due to the arrangement of the connecting rods of the specific ratios, in the operation process of equipment, the equipment cannot collide with the microscope, and the microscope cannot be shielded. In addition, on the basis, due to the RCM structure of the specific ratio in the technical solution, the precision of the equipment during retina tissue puncture can be improved to the 10 μm level, which is far smaller than the diameter of a blood vessel on the retina, the surgery safety and the surgery success rate are greatly improved, and the compactness is greatly improved. In other words, due to the structural design, the movement can be achieved within the range of 10 μm, and accurate positioning of the puncture structure is improved.

Preferably, the length of the seventh connecting rod is 10-50 cm, and the requirements of ophthalmic surgery are met within such size range.

Specifically, in the embodiment, the length of the seventh connecting rod is 30 cm, the length of the first connecting rod 521 is 22.5 cm, the length of the fifth connecting rod 532 is 25 cm, the lengths of the second connecting rod 522 and the sixth connecting rod 533 in the first combined connecting rod 31 are 22.5 cm and 12.5 cm respectively, the lengths of the fourth connecting rod 531 and the third connecting rod 523 in the second combined connecting rod 32 are 25 cm and 30 cm respectively, and the length of the eighth connecting rod is 12.5 cm. The included angle between the second connecting rod 522 and the sixth connecting rod 533 in the first combined connecting rod 31 is 165°, and the included angle between the fourth connecting rod 531 and the third connecting rod 523 in the second combined connecting rod 32 is 165°. It needs to be noted that the measured length of the connecting rods is the distance between hinge points on the connecting rods.

Specifically, in some other embodiments, the length of the seventh connecting rod is 12 cm, the length of the first connecting rod 521 is 9 cm, the length of the fifth connecting rod 532 is 14 cm, the lengths of the second connecting rod 522 and the sixth connecting rod 533 in the first combined connecting rod 31 are 9 cm and 5 cm respectively, the lengths of the fourth connecting rod 531 and the third connecting rod 523 in the second combined connecting rod 32 are 14 cm and 12 cm respectively, and the length of the eighth connecting rod is 5 cm. The included angle between the second connecting rod 522 and the sixth connecting rod 533 in the first combined connecting rod 31 is 158°, and the included angle between the fourth connecting rod 531 and the third connecting rod 523 in the second combined connecting rod 32 is 165°.

Figure 11:
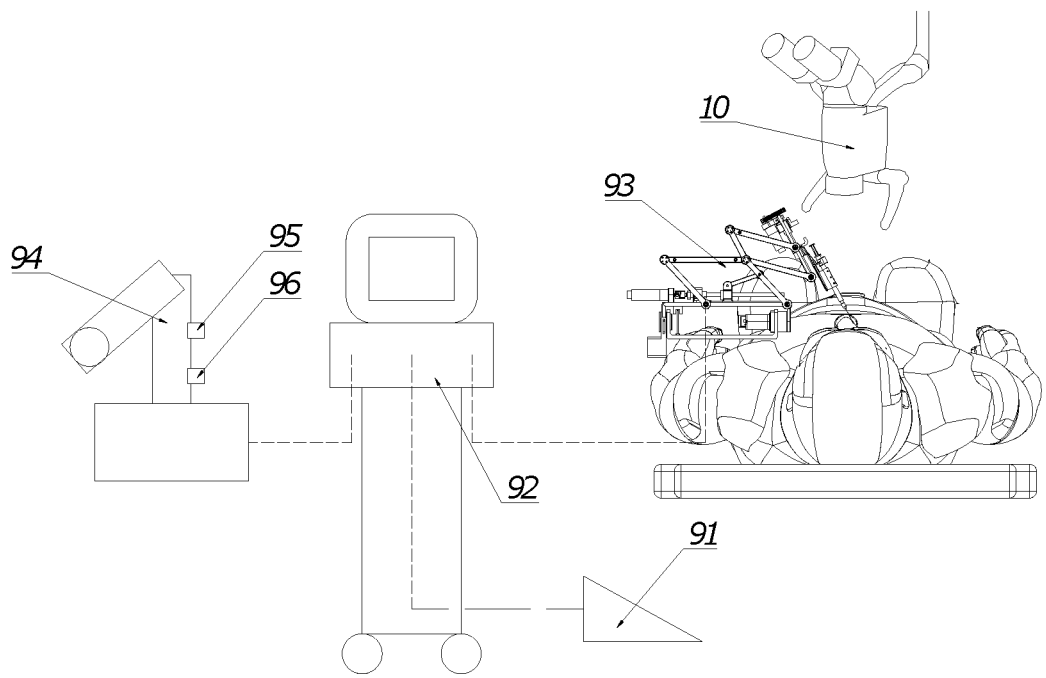
FIG. 11 is a schematic diagram of ophthalmic surgery equipment of the present invention during surgery.

According to the technical solution, as shown in FIG. 11, a schematic diagram (a schematic diagram of ophthalmic surgery equipment during surgery) of the equipment used for performing surgical treatment on the right eye of a patient is shown in the FIG. 11, the equipment is not in contact with the microscope 10 at the moment; if the equipment needs to perform surgical treatment on the left eye of the patient, only the RCM structure needs to be controlled to contract, so that the angle of the instrument 60 is adjusted, and the contracted RCM structure is not in contact with the microscope 10. That is, the equipment only moves in the half space position above the patient in the whole movement process, if the equipment moves in the left half space and does not move in the right half space. According to the technical solution, when the robot cannot treat the left eye or the right eye of the patient, the equipment does not shield the microscope 10, so the technical problem that the microscope 10 needs to be frequently moved is solved.

Preferably, the present invention provides ophthalmic surgery equipment. Referring to FIG. 11, the ophthalmic surgery equipment comprises the surgery robot 93 and a main console 92 matched with the surgery robot 93 for use, wherein the main console 92 can be used for controlling the surgery robot 93 to move, and the main console 92 is connected with the control handle 94; the operator controls the surgery robot 93 to work by operating the control handle 94; the main console 92 is also connected with the pedal 91; the pedal 91 can be used for enabling control of the control handle 94 and the surgery robot 93 and/or speed ratio adjustment of the control handle 94 and the surgery robot 93, such as speed increasing and speed reducing adjustment, thus the operator can conveniently control and select different speed ratios of the control handle 94 in the operating process. What needs to be noted is that the connection not only represents connection through a cable, but also represents data connection; the data connection can be wired or wireless.

Preferably, the surgery robot 93 internally comprises a sensing unit, the sensing unit is used for recognizing the distance between the surgery robot 93 and other objects, especially the distance between the position of the RCM structure on the surgery robot 93 and other objects except the patient, the objects can be regarded as obstacles, for example, the sensing unit is used for recognizing the distance between the RCM structure and the microscope 10, and therefore collision is avoided. When the sensing unit recognizes that the distance between the RCM structure and the microscope 10 is smaller than the preset safety distance, the RCM structure is regarded to be likely to collide with the microscope 10, the control handle 94 vibrates, equipment gives out an alarm sound, and the operator is reminded that collision possibly happens. Further, during vibration, the control handle 94 temporarily shields the function of controlling the surgery robot 93 to move (the shielding time is generally 5-15 seconds), and the situation that during vibration, the operator is frightened, the control handle 94 is greatly driven to move, and consequently the surgery robot 93 moves mistakenly is avoided.

Preferably, the control handle 94 is provided with a button, namely a continuous working button 95. When the handle vibrates, the robot stops moving, the control handle 94 is shielded and waits for an instruction of the operator, and if the operator clicks the continuous working button 95, the robot can continuously move according to the instruction of the control handle 94. It needs to be noted that since the distance between the RCM structure and other objects is smaller than the preset safe distance at the moment, the load of the control handle 94 is increased at the moment, the movement speed of the control handle 94 becomes low, and correspondingly, the movement speed of the RCM structure also becomes low; the control handle 94 is restored to an original control mode until the distance between the RCM structure and other objects is larger than the safe distance.

Preferably, when the distance between the RCM structure and other objects is smaller than the safe distance, the distance between the RCM structure and the other objects is still reduced until the distance between the RCM structure and the other objects is reduced to a preset minimum distance, the control handle 94 is locked at the moment, the control handle 94 still cannot continue to move even under the operation of the operator, and the RCM structure cannot move. At the moment, the equipment gives out a rapid alarm sound, and after a period of time, the control handle 94 returns to the initial position, and the surgery robot 93 also returns to the initial position. (The initial position means that the RCM structure enters a complete contraction state.)

Preferably, the control handle 94 is further provided with a button, namely a route recalculation button 96. When the handle vibrates, the robot stops moving and waits for an instruction of the operator, if the operator clicks the route recalculation button 96, the robot will stop for a period of time (determined according to calculation performance and generally within 1 minute), recalculation is conducted, the tail end 70 of the instrument 60 is located at the same position, but different movement routes are obtained, under the routes, the RCM structure will not touch an obstacle, enough safety distance is reserved, and after the routes are calculated, the routes will be displayed on the main console 92. The operator selects the proper route by himself/herself, then the surgery robot 93 will automatically move according to the calculated route, and the control handle 94 cannot be operated in the process. The robot calculates three different routes at most for the operator to select by himself/herself. When the robot cannot calculate one route meeting the safety distance, the device gives out a rapid alarm sound, and after a period of time, the control handle 94 recovers to the initial position, and the surgery robot 93 recovers to the initial position.

Preferably, the control handle 94 is further provided with a button used for accurately controlling the position of a tail end surgical instrument, for example, a button used for controlling the tail end 70 of the surgical instrument to move forwards by 10 micrometers and/or a button used for controlling the tail end 70 of the surgical instrument to move backwards by 10 micrometers. Accurate control over the surgical tail end can help a doctor to carry out a sub-retinal puncture surgery and an intravascular bypass operation more accurately.

Preferably, the second driving unit 30 further comprises a second power element 12, power input is carried out on the RCM structure through the second power element 12, and motion control over the RCM structure is completed. Specifically, motion of the first quadrilateral structure 52 is controlled through the second power element 12, and therefore the second quadrilateral structure 53 is driven to move, and motion of the instrument 60 is adjusted.

Preferably, the second driving unit 30 does not directly output power to the first quadrilateral structure 52, for example, a rotating shaft or a lifting rod of a motor is directly connected with one side of a first parallel shape, and due to the fact that the direct power output mode is adopted, the precision of the motor completely depends on the precision of the motor; of course, the higher the precision of the adopted motor is, the higher the control precision is, but the problems that the cost is higher, the size is large, and miniaturization of equipment is not facilitated are caused.

Therefore, the present invention does not adopt a direct control mode, but adopts an indirect control mode. The specific mode is that the second power element 12 is in power connection with a first lead screw 510 through a first coupling 511; a first sliding block 13 is arranged on the first lead screw 510; a driving rod 80 is hinged to the first sliding block 13; one end of the driving rod 80 is hinged to the first sliding block 13, and the other end of the driving rod 80 is hinged to a certain position on the first quadrilateral structure 52, so that the second power element 12 can drive the first quadrilateral structure 52 to move. In the driving process, the lead screw mode is adopted, so the movement precision can be improved, the requirement on the second power element 12 is reduced, the size of the second power element 12 is also reduced, and the cost is reduced. In addition, the self-locking characteristic and the counterweight function of the mechanism structure can be utilized, thus an RCM structure cannot collapse under the condition of sudden power failure, and the damage of the instrument 60 to the patient in the surgery process is avoided.

Preferably, one end of the driving rod 80 is hinged to the first sliding block 13, and the other end of the driving rod 80 is connected to the fourth supporting rod 58 and is in running fit connection with the middle position of the fourth supporting rod 58.

Third Driving Unit

The third driving unit 40 is mounted on the tail end mounting frame 534.

The third driving unit 40 is used as a three-stage power unit and directly drives the instrument 60 to move; in order to conveniently control the instrument 60, the third driving unit 40 is not suitable for being set to be in rotary control and is in simpler linear control; the simple linear control is the most convenient and direct to control the tail end 70. Specifically, a second screw rod 71 is arranged on the tail end mounting frame 534; a second slide block 18 is mounted on the second screw rod 71; the instrument 60 is mounted on the second slide block 18. The second screw rod 71 drives the second slide block 18 to move so as to control the movement of the instrument 60.

Preferably, the second lead screw 71 is driven by a third power element 14, but the mode that the third power element 14 is directly connected is not adopted, and the mode that the third power element 14 is indirectly connected through the gear set is adopted. The mode has the advantages that 1, the third power element 14 and the second lead screw 71 are not located on the same straight line, and the overall length of the third driving unit 40 can be reduced; and 2, the third power element 14 can be mounted on the back face of the tail end mounting frame 534 through the gear set, in this way, the third power element 14 is mounted between two RCM structures (between two sets of connecting rods), the space utilization rate is increased, and the mode is very useful for reducing the size of equipment. Specifically, the power output end of the third power element 14 is connected with a first gear 74, the first gear 74 is meshed with a second gear 75, and the axis position of the second gear 75 is connected with the second lead screw 71 through a coupling.

Instrument Holding Device

An instrument 60 is mounted on the third driving unit 40 through an instrument holding device, so that the instrument 60 can be controlled through the third driving unit 40.

Figure 4:
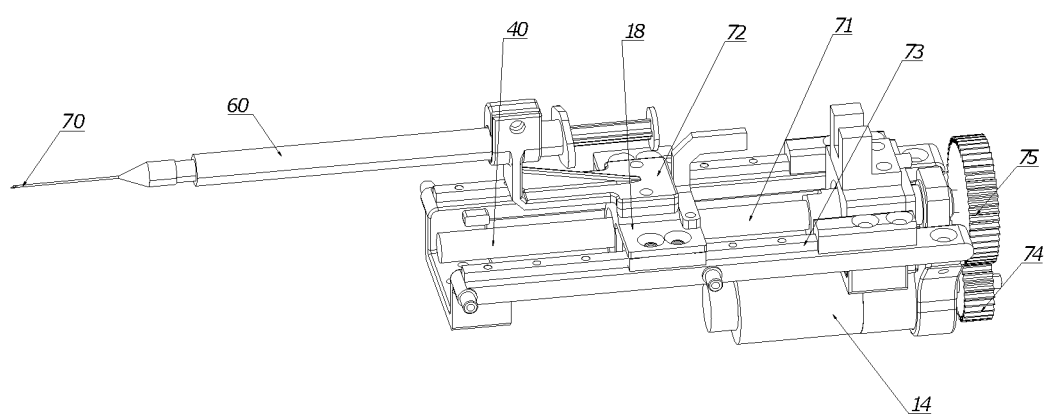
FIG. 4 is a structural schematic diagram of a third driving unit of the present invention.
Figure 5:
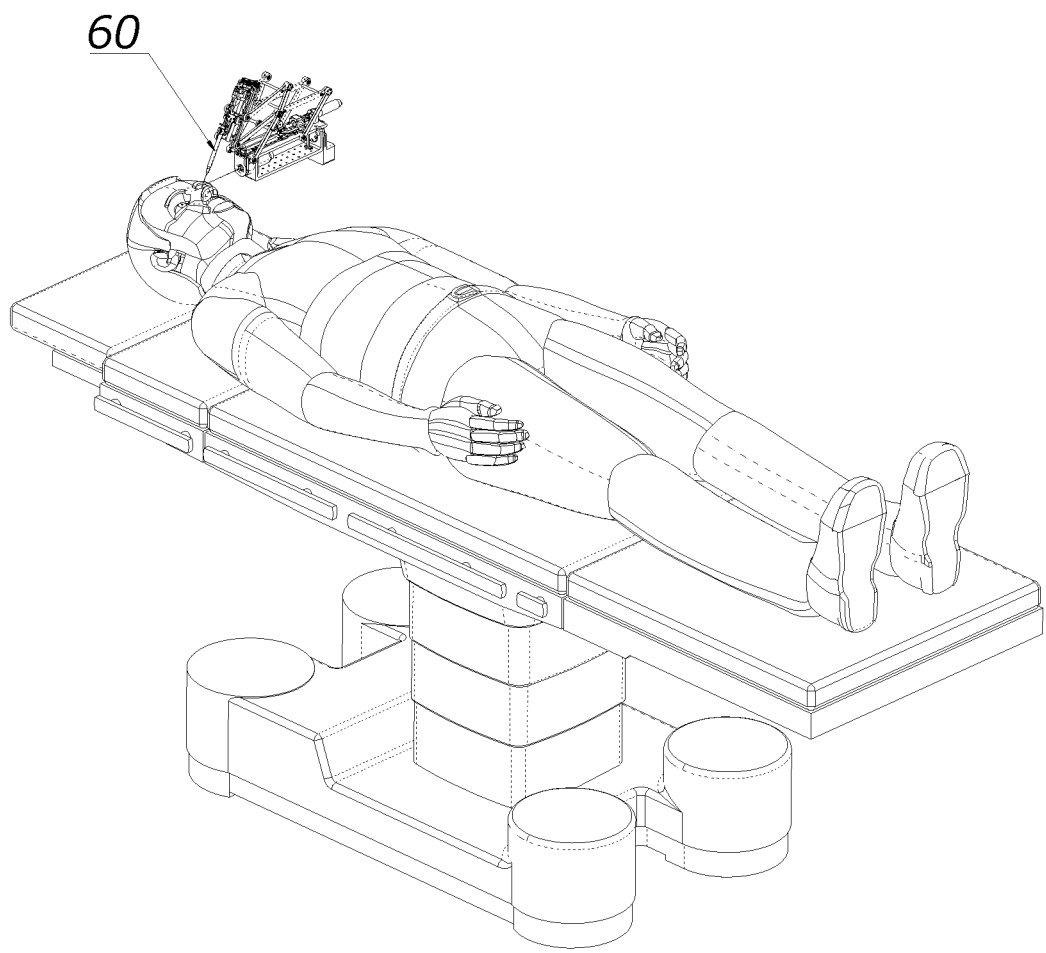
FIG. 5 is a schematic diagram of equipment of the present invention during working.

The instrument holding device can be immovable, thus the instrument 60 can be fixedly mounted on the third driving unit 40. For example, as disclosed in FIG. 4, the instrument holding device is an instrument mounting bracket 72, and the instrument mounting bracket 72 is used for mounting the instrument 60. At the moment, the instrument 60 completely moves along with the movement of the first driving unit 20, the second driving unit 30 and the third driving unit 40, and does not have the ability of autonomous movement.

Figure 13:
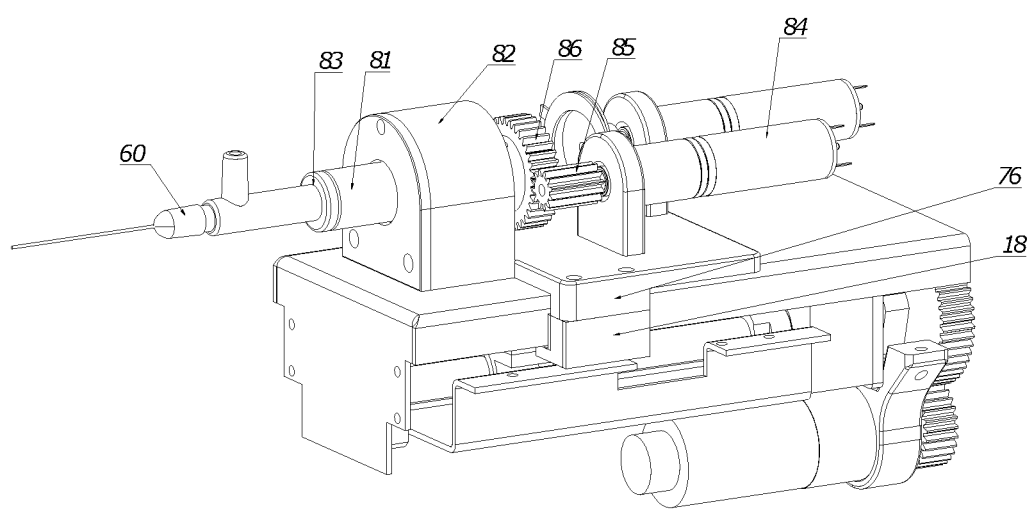
FIG. 13 is a structural schematic diagram of an instrument holding device during fixation of an injector.

The instrument holding device can be movable, thus the instrument 60 is also movable when being mounted on the instrument holding device, namely the instrument 60 is movably mounted on the third driving unit 40. For example, the instrument holding device, as shown in the FIG. 13, comprises a mounting unit 81 and a fixing unit 82, wherein the mounting unit 81 is used for mounting the instrument 60 and the mounting unit 81 is rotatably connected into the fixing unit 82; for example, a bearing is arranged in the fixing unit 82, and the fixing unit 82 is connected with the mounting unit 81 through the bearing, so that the instrument 60 can be driven to rotate through the rotation of the mounting unit 81. Further, the instrument 60 is detachably connected with the mounting unit 81, for example, a mounting hole 83 for mounting the instrument 60 is formed in the mounting unit 81, and the instrument 60 is inserted into the mounting hole 83, so that the mounting of the instrument 60 is completed. Further, a locking hole 90 for fastening the instrument 60 is formed in the mounting unit 81, and an angle of 90° is formed between the axial direction of the locking hole 90 and the axial direction of the mounting hole 83; a bolt is fixed in the locking hole 90 so that the instrument 60 can be fastened when the bolt is abutted against the instrument 60.

Figure 14:
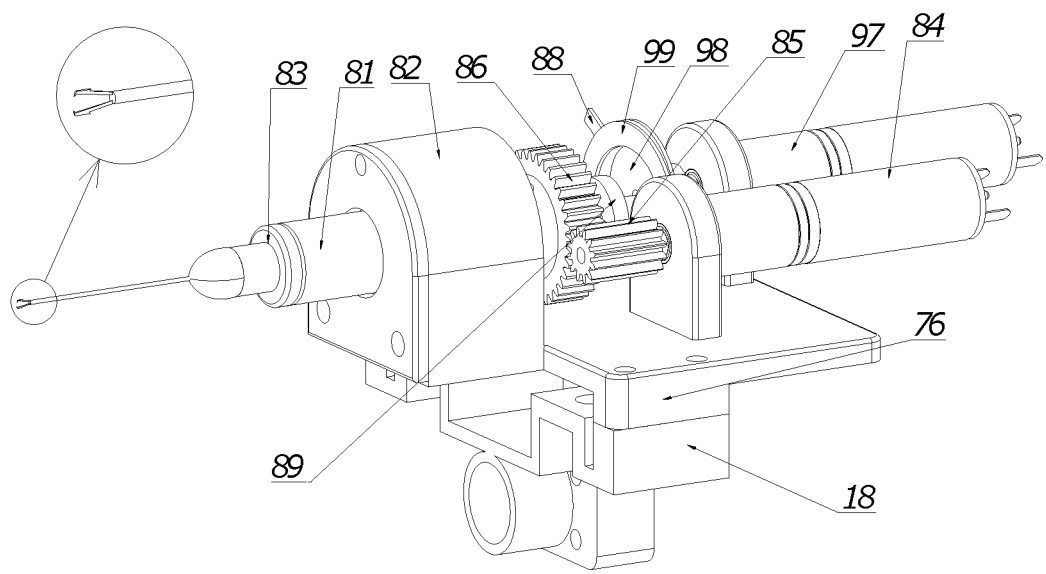
FIG. 14 is a structural schematic diagram of an instrument holding device during fixation of forceps.
Figure 15:
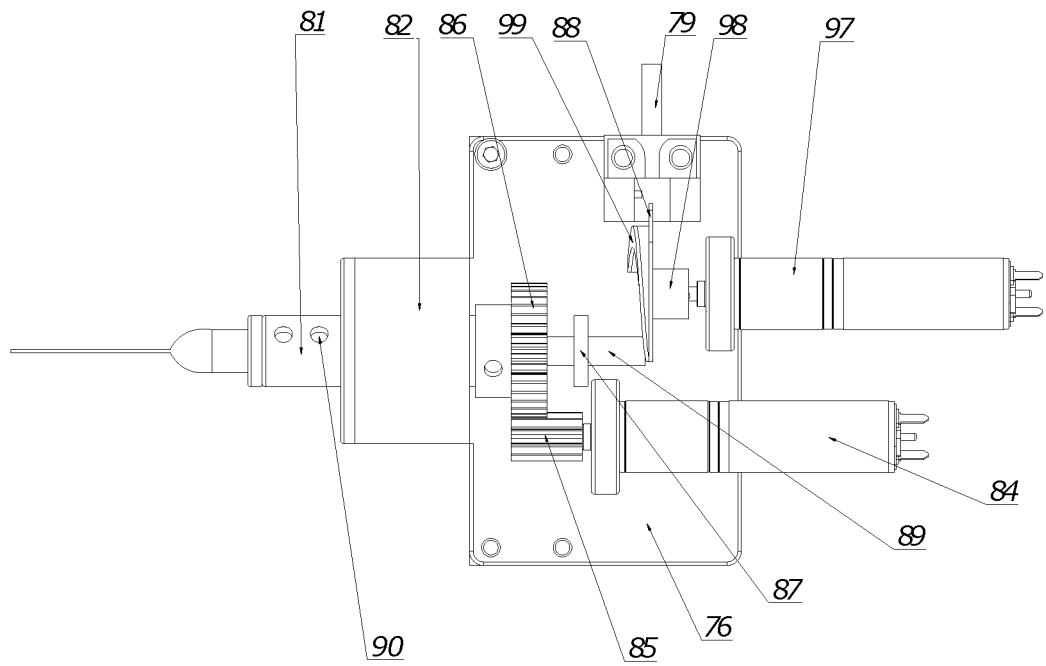
FIG. 15 is a top view of FIG. 14.

Preferably, the instrument 60 can be a surgery element or other used articles, and the surgery element can be an injector or forceps. For example, as shown in the FIG. 13, the injector is fixed to a mounting unit 81; for example, as shown in the FIG. 14, the forceps are fixed to the mounting unit 81.

Preferably, the instrument holding device further comprises a first power unit, the first power unit can provide rotating power for the mounting unit 81, and the instrument 60 can rotate together through the power. The first power unit comprises a fourth power element 84 and a first gear 85 connected with the fourth power element 84, and a second gear 86 is arranged on the mounting unit 81 and meshed with the first gear 85. Further, one end of the mounting unit 81 is used for being connected with the instrument 60, and the other end of the mounting unit 81 is connected with the second gear 86.

When instruments 60 fixed to the instrument holding device are some special instruments, the special instruments need an additional power unit to be driven, for example, forceps need an additional power unit to drive themselves to complete clamping and loosening operation. (Surgical forceps are finished products purchased on the market and have resilience force, when the ends of the forceps are subjected to force, the forceps are clamped, and when the force disappears, the forceps are loosened.) Preferably, the instrument holding device further comprises a second power unit, the second power unit is used for providing additional force for the forceps, a through hole is formed in the mounting unit 81, and the acting force of the second power unit can directly act on the forceps mounted in the mounting unit 81 through the through hole. More specifically, the second power unit comprises a fifth power element 97, the fifth power element 97 is connected with a propelling wheel 98, protrusions 99 different in height are arranged on the propelling wheel 98, the ejector rod 89 is arranged at the positions of the protrusions 99 on the propelling wheel 98 in an abutting mode, and the ejector rod 89 extends into the through hole of the mounting unit 81 and can abut against the forceps. The propelling wheel 98 is driven by the fifth power element 97 to rotate, the protrusions 99 at different positions on the propelling wheel 98 abut against the ejector rod 89, due to the fact that the protrusions 99 at different positions are different in height, the protrusions 99 on the propelling wheel 98 can provide different strokes for the ejector rod 89 when rotating, and the elastic forceps are clamped and loosened by extruding.

Preferably, a baffle 87 is arranged on the ejector rod 89, and the minimum diameter of the baffle 87 is larger than the maximum diameter of the through hole of the mounting unit 81 so that the baffle 87 can prevent the ejector rod 89 from being completely embedded into the through hole.

Preferably, the protrusions 99 on the propelling wheel 98 are in a gradual change form, and the height of the protrusions 99 is gradually increased or gradually decreased along with rotation of the propelling wheel 98.

Preferably, instrument holding device further comprises a limiting structure, and the limiting structure is used for limiting the rotating angle of the propelling wheel 98, so that excessive rotation of the propelling wheel 98 is avoided. The limiting structure comprises a blocking piece 88 arranged on the propelling wheel 98 and a matched photoelectric switch 79.

When the instrument 60 fixed to the instrument holding device is an injector, no extra power unit is needed at the moment. Preferably, the ejector rod 89 is detachable, and after the ejector rod 89 is detached, power connection between the fifth power element 97 and the instrument 60 is cut off.

Preferably, the instrument holding device further comprises a mounting plate 76, parts in the instrument holding device can be mounted on the mounting plate 76, the mounting plate 76 is connected with the second sliding block 18, and therefore when the third driving unit controls the second sliding block 18 to move, the instrument 60 in the instrument holding device can be driven to move.

According to the above technical solution, the first power element 21, the second power element 12, the third power element 14, the fourth power element 84 and the fifth power element 97 can be traditional power elements such as a motor. Preferably, the first power element 21, the second power element 12, the third power element 14, the fourth power element 84 and the fifth power element 97 are matched with encoders, and the encoders can be used for recording the speed of a rotor, the position of the rotor, the mechanical position and other parameters. For example, a first encoder 22 is mounted on the first power element 21.

Preferably, the robot is provided with photoelectric switches or other limiting structures for the first driving unit 20, the second driving unit 30 and the third driving unit 40, and excessive movement of all positions is avoided.

The foregoing description only describes the specific embodiments of the present invention, but the protection scope of the present invention is not limited to this. Any changes or substitutions that are thought of without creative work should fall within the scope of protection of the present invention. Therefore, the scope of protection of the present invention should be defined by the protection scope claimed by the appended claims.

All patents and publications mentioned in the Specification of the present invention are public technologies in the art and can be used in the present invention. All patents and publications cited herein are also listed in the references, as if each publication is specifically and separately cited. The present invention described herein can be implemented in the absence of any one element or multiple elements and in the presence one restriction or multiple restrictions, and such restriction is not specifically stated herein. For example, the terms "comprising", "substantially consisting of" and "consisting of" in each example herein can be replaced by one of the remaining two terms. The so-called "one" herein only means "one", and it does not rule out that only one is included, and it may also mean that two or more are included. The terms and expressions used herein are described without limitation. There is no intention to indicate that the terms and explanations described in this Specification exclude any equivalent features. However, it can be understood that any appropriate changes or modifications can be made within the scope as claimed in the appended claims of the present invention. It can be understood that the examples described herein are some preferred embodiments and features. Any ordinary person skilled in the art can make some changes and modifications based on the essence of the description of the present invention. These changes and modifications are also considered to fall within the scope of the present invention and the scope claimed by the appended independent claims and dependent claims.

The invention claimed is:

1. A robotic assisted system for ophthalmic surgery, comprising a first driving unit, a second driving unit and a third driving unit, wherein the three driving units can respectively complete the movement in three dimensions, the first driving unit is connected with the second driving unit, the second driving unit is connected with the third driving unit, and an instrument assembly for performing ophthalmic surgery is arranged on the third driving unit;

wherein, the third driving unit can drive the instrument assembly to move, the second driving unit can drive the third driving unit and instruments thereon to move, and the first driving unit can drive the second driving unit, the third driving unit on the second driving unit and the instruments on the third driving unit to move;

the accurate control on the instruments can be completed by controlling the three different driving units, wherein the first driving unit can provide rotation motion in one direction, and wherein the first driving unit is provided with a first speed reducer in a matched mode, and the first speed reducer is mounted between the connecting piece and the first power element; the first speed reducer is a harmonic speed reducer; wherein the base is in a U shape, the two ends of the pedestal are connected to the U-shaped base through connecting pieces, the connecting position on one side is provided with power output of the first power element, and the connecting position on the other side is provided with a bearing; a balancing weight is mounted on the connecting piece close to one side of the bearing.

2. The robotic assisted system for ophthalmic surgery according to claim 1, wherein the first driving unit comprises a base, a first power element is mounted on the base, the output end of the first power element is connected with a connecting piece, the connecting piece is connected with a pedestal, the pedestal is used for being mounted on a second driving element, and the pedestal can rotate by controlling the first power element to rotate.

3. The robotic assisted system for ophthalmic surgery according to claim 1, wherein the second driving unit comprises an RCM structure, the structure comprises a first quadrilateral structure and a second quadrilateral structure, wherein the first quadrilateral structure and the second quadrilateral structure have a common overlapping vertex, the vertex defines two sides of the first quadrilateral structure and two sides of the second quadrilateral structure, the first quadrilateral structure comprises a second connecting rod and a third connecting rod which are located at the position of the overlapping vertex and connected with the overlapping vertex, and the second quadrilateral structure comprises a fourth connecting rod and a sixth connecting rod which are located at the position of the overlapping vertex and connected with the overlapping vertex; wherein, the third connecting rod and the fourth connecting rod are integrally formed, and the sixth connecting rod and the second connecting rod are integrally formed.

4. The robotic assisted system for ophthalmic surgery according to claim 3, wherein the first quadrilateral structure comprises a second connecting rod, a third connecting rod, a first connecting rod and a seventh connecting rod, wherein the second connecting rod and the third connecting rod are connected and hinged through overlapped vertexes, the third connecting rod and the first connecting rod are connected and hinged through a first vertex; the seventh connecting rod comprises a base, the base is hinged to the second connecting rod and the first connecting rod respectively, the hinged positions are a second vertex and a third vertex respectively, the part, positioned between the second vertex and the third vertex, on the base is the seventh connecting rod.

5. The robotic assisted system for ophthalmic surgery according to claim 4, wherein the second quadrilateral structure comprises a sixth connecting rod, a fourth connecting rod, a fifth connecting rod and an eighth connecting rod, the fourth connecting rod and the sixth connecting rod are connected and hinged through overlapped vertexes, the fifth connecting rod and the sixth connecting rod are connected and hinged through a fourth vertex, the eighth connecting rod comprises a tail end mounting frame, the tail end mounting frame is hinged to the fourth connecting rod and the fifth connecting rod respectively, the hinged positions are a fifth vertex and a sixth vertex respectively, the part, positioned between the fifth vertex and the sixth vertex, on the tail end mounting frame is the eighth connecting rod.

6. The robotic assisted system for ophthalmic surgery according to claim 5, wherein the second driving unit comprises at least one group of RCM structures consisting of the first quadrilateral structure and the second quadrilateral structure, and the RCM structures move synchronously; in two adjacent groups of RCM structures, corresponding connecting rods are connected through supporting rods; or, a connecting plate for connecting the connecting rods is arranged between the corresponding connecting rods, and the connecting plate and the corresponding connecting rod are integrally formed; wherein, the second driving unit further comprises a second power element, power input is performed on the RCM structures through the second power element to complete motion control of the RCM structures, and the motion of the first quadrilateral structure is controlled through the second power element, such that the motion of the second quadrilateral structure is driven, and the motion of the instrument is adjusted.

7. The robotic assisted system for ophthalmic surgery according to claim 6, wherein the second power element is in power connection with a first lead screw through a first coupling, a first sliding block is arranged on the first lead screw, a driving rod is hinged to the first sliding block, one end of the driving rod is hinged to the first sliding block, and the other end of the driving rod is hinged to a certain position on the first quadrilateral structure, such that the second power element can drive the first quadrilateral structure to move.

8. The robotic assisted system for ophthalmic surgery according to claim 7, wherein the length of the third connecting rod is the same as that of the seventh connecting rod; the ratio of the length of the first connecting rod to the seventh connecting rod is between ½ and ⅞, the length of the first connecting rod is the same as that of the second connecting rod; the ratio of the length of the sixth connecting rod to the second connecting rod is between ¼ and ¾, the length of the distance of the part positioned between the fifth vertex and the sixth vertex on the tail end mounting frame is the same as that of the sixth connecting rod; the ratio of the length of the fourth connecting rod to the third connecting rod is between ¾ and ¹¹⁄₁₂, and the length of the fifth connecting rod is the same as that of the fourth connecting rod.

9. The robotic assisted system for ophthalmic surgery according to claim 8, wherein the angle between the second connecting rod and the sixth connecting rod in the first combined connecting rod is 120°-175°, and the angle between the fourth connecting rod and the third connecting rod in the second combined connecting rod is 120°-175°.

10. The robotic assisted system for ophthalmic surgery according to claim 1, wherein the third driving unit is mounted on the tail end mounting frame, and the third driving unit can perform linear control on the instrument; a second screw rod is arranged on the tail end mounting frame, a second sliding block is mounted on the second screw rod, an instrument mounting bracket is mounted on the second sliding block, and the instrument mounting bracket is used for mounting the instrument; the second screw rod is driven by a third power element, and the third power element is indirectly connected through a gear set; the power output end of the third power element is connected with a first gear, the first gear is meshed with a second gear, and the axis position of the second gear is connected with the second screw rod through a coupling.

11. The robotic assisted system for ophthalmic surgery according to claim 1, wherein a surgery robot comprises a sensing unit, and the sensing unit is used for identifying the distance between the RCM structure position on the surgery robot and other objects except a patient.

12. The robotic assisted system for ophthalmic surgery according to claim 1, wherein the system further comprises a main console, the main console can be used for controlling the surgery robot to move, the main console is connected with a control handle, an operator controls the surgery robot to work by operating the control handle, the main console is further connected with a pedal, and the pedal can be used for enabling control over the control handle and the surgery robot and/or speed ratio adjustment of the control handle and the surgery robot.

13. The robotic assisted system for ophthalmic surgery according to claim 11, wherein the system further comprises a sensing unit, the sensing unit is used for identifying the distance between the position of the RCM structure on the surgery robot and other objects except a patient, the surgery robot is provided with a safe distance, when the sensing unit identifies that the distance between the RCM structure and an obstacle is smaller than a preset safe distance, the control handle vibrates and/or equipment gives out an alarm, and meanwhile the control handle temporarily shields the function of controlling the surgery robot to move.

14. A robotic assisted system for ophthalmic surgery, comprising a first driving unit, a second driving unit and a third driving unit, wherein the three driving units can respectively complete the movement in three dimensions, the first driving unit is connected with the second driving unit, the second driving unit is connected with the third driving unit, and an instrument assembly for performing ophthalmic surgery is arranged on the third driving unit;

wherein the third driving unit can drive the instrument assembly to move, the second driving unit can drive the third driving unit and instruments thereon to move, and the first driving unit can drive the second driving unit, the third driving unit on the second driving unit and the instruments on the third driving unit to move, the accurate control on the instruments can be completed by controlling the three different driving units, wherein a surgery robot comprises a sensing unit, and the sensing unit is used for identifying the distance between the RCM structure position on the surgery robot and other objects except a patient, wherein the system further comprises a sensing unit, the sensing unit is used for identifying the distance between the position of the RCM structure on the surgery robot and other objects except a patient, the surgery robot is provided with a safe distance, when the sensing unit identifies that the distance between the RCM structure and an obstacle is smaller than a preset safe distance, the control handle vibrates and/or equipment gives out an alarm, and meanwhile the control handle temporarily shields the function of controlling the surgery robot to move, and wherein the control handle is provided with a button, namely a continuous working button, when the handle vibrates and/or the equipment gives out an alarm, the robot stops moving, the control handle is shielded, and if an operator clicks the continuous working button, the surgery robot can continue to move according to a command of the control handle.

15. The robotic assisted system for ophthalmic surgery according to claim 14, wherein when the distance between the RCM structure and other objects is smaller than the preset safety distance, the load of the control handle is increased, the movement speed of the control handle is decreased, and correspondingly, the movement speed of the RCM structure is decreased; when the distance between the RCM structure and other objects is larger than the safety distance, the control handle restores an original control mode.

16. The robotic assisted system for ophthalmic surgery according to claim 15, wherein the surgery robot has a minimum distance, the minimum distance is smaller than the safe distance, when the distance between the RCM structure and other objects is smaller than or equal to the preset minimum distance, the control handle is locked, the control handle cannot continue to move under the operation of the operator, and the RCM structure cannot move;

meanwhile, the equipment gives an alarm, after a period of time, the control handle returns to the initial position, and the surgery robot returns to the initial position.

17. The robotic assisted system for ophthalmic surgery according to claim 14, wherein the control handle is provided with a button, namely a route recalculation button, when the handle vibrates and/or the equipment gives out an alarm sound, the surgery robot stops moving and waits for an instruction of the operator, if the operator clicks the route recalculation button, the robot stops for a period of time and recalculates different movement routes when the tail ends of instruments are located at the same position; under the routes, the RCM structure does not touch the obstacle and enough safety distance is kept.

18. The robotic assisted system for ophthalmic surgery according to claim 14, wherein when the robot cannot calculate one route meeting the safety distance, the equipment gives out the rapid alarm sound, after a period of time, the control handle is recovered to an initial position and the surgery robot is also recovered to the initial position.

* * * * *